United States Patent
Benattar et al.

(10) Patent No.: US 9,062,069 B2
(45) Date of Patent: Jun. 23, 2015

(54) ESTERS OF N-ACYLATED DERIVATIVES OF AMINO ACIDS AND ISOSORBIDE, METHOD FOR PREPARING SAME, AND USE THEREOF IN COSMETICS AND AS DRUG

(75) Inventors: Andre Benattar, Castres (FR); Laetitia Cattuzzato, Castres (FR); Sandy Dumont, Caucalieres (FR); Stephanie Garcel, Castres (FR); Jerome Guilbot, Castres (FR); Sebastien Kerverdo, Vincennes (FR); Herve Rolland, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 14/126,137

(22) PCT Filed: May 24, 2012

(86) PCT No.: PCT/FR2012/051167
§ 371 (c)(1),
(2), (4) Date: Dec. 13, 2013

(87) PCT Pub. No.: WO2013/001192
PCT Pub. Date: Jan. 3, 2013

(65) Prior Publication Data
US 2014/0135373 A1    May 15, 2014

(30) Foreign Application Priority Data
Jun. 30, 2011 (FR) .................... 11 55900

(51) Int. Cl.
| | |
|---|---|
| *C07D 493/04* | (2006.01) |
| *A61K 31/4025* | (2006.01) |
| *A61K 31/34* | (2006.01) |
| *A61Q 19/00* | (2006.01) |
| *A61K 8/42* | (2006.01) |
| *A61K 8/49* | (2006.01) |
| *A61Q 19/08* | (2006.01) |

(52) U.S. Cl.
CPC .............. *C07D 493/04* (2013.01); *A61Q 19/00* (2013.01); *A61K 8/42* (2013.01); *A61K 8/4913* (2013.01); *A61K 8/4973* (2013.01); *A61Q 19/08* (2013.01); *A61K 31/34* (2013.01); *A61K 31/4025* (2013.01)

(58) Field of Classification Search
None
See application file for complete search history.

(56) References Cited

PUBLICATIONS

Muri, et al., Amino Acids, 27:153 (2004).*

* cited by examiner

*Primary Examiner* — Michael Barker
(74) *Attorney, Agent, or Firm* — Young & Thompson

(57) ABSTRACT

Compound with formula (I), wherein R' and R" represent a hydrogen atom, a monovalent radical with formula (IIa), or a monovalent radical with formula (IIb), it being understood that at least one of the R' or R" radicals does not represent a hydrogen atom and that when the R' and R" radicals do not represent a hydrogen atom, R' and R" are identical; method for preparing and using in cosmetics and as a drug.

16 Claims, No Drawings

ESTERS OF N-ACYLATED DERIVATIVES OF AMINO ACIDS AND ISOSORBIDE, METHOD FOR PREPARING SAME, AND USE THEREOF IN COSMETICS AND AS DRUG

This invention relates to new chemical products and new chemical compositions intended for the prevention and/or treatment of visible signs of dysfunctions of the venous system and/or alteration to vascular permeability of the human skin.

Human skin forms the first image offered to others, and consequently an improvement to the skin is a subject of constant concern for human beings. Skin is the reflection of a state of well-being, frequently associated with youth, or on the other hand a state of fatigue and/or aging.

Good functioning of blood microcirculation is one essential factor necessary for a good state of skin aesthetics. The aging phenomenon is usually the result in a reduction in the number, size and functionality of dermal vessels responsible for functioning of blood microcirculation, that tend to become less numerous and more brittle.

This rarefaction of subcutaneous capillary vessels reduces oxygenation of the skin and reduces the input of nutrients (trace elements and vitamins), which in an elderly human being results in a chronic facial paleness (bibliographic references (1), (2) and (3)). Similarly, any dysfunction of the venous system characterised by a reduction in blood circulation, causes the same insufficient tissue oxygenation phenomenon known as hypoxia.

The concept of vascular permeability describes the role played by small blood vessels (arterioles, venules and microvessels) to perform a barrier function between blood circulating in said small blood vessels and tissues, and more particularly skin tissues. When vascular permeability deteriorates due to the effect of aging and/or inflammatory phenomena and/or external stress phenomena, the tissues then in a hypoxia situation become inflamed, which causes the appearance of exacerbated rash phenomena that can lead to the formation of oedema on the skin zone concerned. Vessels may also expand or even break, causing the formation of telangiectasis.

The endothelium is a tissue that performs the primary function of containing blood inside blood vessels, while enabling the exchange of nutrient substances with the internal medium. It is composed of endothelial cells and muscular cells that act as molecular "filters" to enable this exchange of nutrient substances, the function of which is to control blood coagulation and vasomotricity of an individual. Humoral mediators, hormones, cytokines and growth factors form biochemical constraints that act on activation of endothelial cells. Endothelial cells are sensitive to oxidation stress caused by an increased presence of oxygenated derivatives, for example such as superoxide ions, hydrogen peroxides, hydroxyl radicals that go beyond the regulating capabilities of the natural anti-oxidant system (superoxidismutase, catalase, etc.) that in particular reduces available oxygen in endothelial cells, namely a hypoxia phenomenon of said endothelial cells and consequently a reduction in the production of Adenine TriPhosphate (ATP) in said endothelial cells.

According to the literature (bibliographic reference (4)) Janssens, "*effect of venotropic drugs on the respiratory activity of isolated mitochondria and in endothelial cells*", in British Journal of Pharmacology (2000) 130, 1513-1524), venous insufficiencies caused by dysfunction of the venous system and/or alteration to vascular permeability that results in a reduction of the arterial blood supply to an organ (ischemia), which essentially causes a reduction in oxygenation of the tissues of the organ to less than it needs to put it in a hypoxia situation, consequently causing a reduction in the production of ATP by endothelial cells.

Depending on the organisation of endothelial cells in the organs, the endothelium performs a function specific to said organ. Consequently, when they are subjected to a mechanical or biochemical constraint, endothelial cells generate responses to different natures of stimuli (exposure to ultraviolet radiation, large temperature and/or humidity variations, pollution, etc.) that have different macroscopic consequences. Thus, a dysfunction of the venous system and/or an alteration to vascular permeability generated and/or exacerbated by mechanical and/or biochemical constraints, can create a hypoxia situation in the region around the contour of the eye resulting in the appearance of a non-inflammatory type of oedema, and particularly by the appearance of dark circles and/or bags under the eyes, or in the lower members, by the appearance of feeling of heaviness in the legs resulting particularly in swelling of the calves and/or feet and/or ankles.

The region around the contour of the eye is characterised by dense innervation and thin skin, poor in cutaneous lipids, then becoming very sensitive to external stress (state of fatigue, lack of sleep, exposure to UV, tobacco, alcohol, etc.) and to different mechanical and biochemical constraints. Dysfunctions of the venous system and/or alteration to vascular permeability that result in vasodilatation or congestion of blood capillaries in this particular zone around the contour of the eye are also more visible due to the thinness of the skin. When vasodilatation or congestion of blood capillaries present under the eyes are lasting, these phenomena create persistent sensations of discomfort and cause the appearance of dark circles and/or bags under the eyes that are then inaesthetic. Skin aging also results in a reduction in the number, size and functionality of dermal vessels, which causes a reduction in nutrient input and radiance of the complexion. These phenomena are also strengthened by slower lymphatic circulation in this zone around the contour of the eye.

The phenomenon or the sensation of heaviness in the lower members and particularly the "heavy legs" phenomenon is experienced by persons who experience dysfunctions of the venous system and/or an alteration to the vascular permeability, triggered or aggravated by factors related to heredity, sedentarity or a prolonged standing position, exposure to heat or abuse of tobacco or alcohol. This phenomenon is characterised by expansion of the veins, and results in the appearance of pain, tingling and swelling of the calf, feet and ankles.

Therefore there is a need for satisfactory solutions to prevent and/or treat reductions in the production of ATP by endothelial cells under the effect of oxidising stress so as to prevent and/or treat dysfunctions of the venous system and/or alteration to vascular permeability resulting in hypoxia of endothelial cells in the human body and inaesthetic effects, for example such as dark circles and/or bags under the eyes and the "heavy legs" phenomenon.

Makeup products offer a solution to mask or attenuate apparent defects in the skin and can provide a solution to the presence of dark circles and bags in the peri-ocular zone. Foundations give a matte appearance to the skin and allow its colour to be evened out. But these cosmetic solutions can only treat the visible consequences of dysfunctions of the venous system or alteration to vascular permeability in the zone around the eyes, without treating their causes. Furthermore, the use of these makeup compositions has the disadvantage that they introduce an unnatural appearance to the skin and some are difficult to spread and can cause drying of the skin in the long term.

Another solution consists of encouraging the production of nitrogen monoxide by mitochondria of cells subject to the hypoxia phenomenon. Nitrogen monoxide is a known molecule that is released particularly by endothelial cells to provoke the vasodilatation phenomenon and consequently an increase in the blood flow. International publication WO2008/141296A1 discloses a method of treating hypoxia of mammal tissues by exposing said tissues to electromagnetic radiation in the visible part of the light spectrum so as to encourage the production of nitrogen monoxide by mitochondria of tissues exposed to this radiation. Publication FR 2 883 171 A1 discloses the use of agents facilitating the production of nitrogen monoxide in and/or on the skin chosen from among nitrogen monoxide donors or precursors (for example such as compounds comprising nitro or nitroso substituents, oximes, hydroxylamine, N-hydroxy guanidine and its salts, nitrosylated transition metals, etc.), agents enabling non-polymeric release of nitrogen monoxide in the organism (for example amino acids peptides), agents for stimulation of synthesis and/or the nitrogen monoxide synthase (NOS) activity, for example such as interleukins, lipopolysaccharides, L-glutamic acid, arachidonic acid. However, this approach through the use of solutions aimed at generating an increase in the production of nitrogen monoxide in the organism does have the disadvantages that it only concerns stimulation of the vasodilatation phenomenon and it induces risks of deregulating the vasodilatation/vasoconstriction balance; the alternation and equilibrium of the two phenomena have to be respected to maintain and/or achieve balanced functioning of the venous system and/or vascular permeability.

Another solution consists of chelating $Fe^{3+}$ ions present in the hemosiderine that is a pigment resulting from degradation of haemoglobin accumulated in capillary vessels due to slowing of blood microcirculation in the peri-ocular region. International publication WO2008035152 A1 discloses several efficient ferric ion chelating agents that do not create any ocular irritation problems during application of a formulation containing them on the zone to be preserved or treated.

These agents include 3-hydroxy-2-methyl-4-pyrone (or maltol), ethyl maltol, octopirox, ciclopirox, rilopirox, gallic acid, esters of gallic acid, kojic acid and derivatives of kojic acid. Apart from the fact that this solution uses compounds either mixed in vegetable extracts or obtained following multi-step methods not adapted to the cosmetic industry, it can only treat the apparent consequences of dysfunctions of the venous system or alteration to vascular permeability and only on the peri-ocular zone, without treating their causes.

International publication WO2011/059866 discloses monoalkanoyl and dialkanoyl derivatives of isosorbide and the use of cosmetic compositions comprising such compounds to reduce manifestations of aging of mammal skin, for example atrophy of the skin of said mammals, and to prevent or delay the appearance of dark circles around the eyes.

Japanese patent application No 2000-229921 discloses the use of polyol esters of N-acylamino acids as being efficient surface active agents (paragraph [0003] in said application). International publication WO2010034917 discloses mono-esters and di-esters of N-(ω-undecylenoyl)phenylalanine polyols and their uses as agents to make the human skin lighter.

The literature (bibliographic reference (5) M. Okada et al., J. Appl. Polym. Sci., 2001, 81(11), pages 2721-2734, and bibliographic reference (6) Z. Gomurashvili et al., J. Macromol. Sci., Pure Appl. Chem., 2000, A37(3), 215-227) discloses the synthesis of polymers obtained by polycondensations of p-toluene acid salts of isohexide derivatives with esters of dicarboxylic acids.

To our knowledge, no ester of N-acyl aminoacid derivatives has been described as being capable of preventing and/or treating reductions in the production of ATP by endothelial cells subjected to oxidising stresses. Consequently, to our knowledge, no ester of N-acyl aminoacid derivatives has been described as being capable of preventing and/or treating dysfunctions of the venous system and/or alteration to vascular permeability. Similarly to our knowledge, no ester of N-acyl amino acid derivatives has been described as being capable of preventing the appearance and/or reducing inaesthetic effects generated by hypoxia of endothelial cells of the human body, as for example dark circles around and/or bags under the eyes, and the "heavy legs" phenomenon.

Therefore, the applicant has attempted to develop a new technical solution consisting of new esters of N-acyl aminoacid derivatives to prevent and/or slow the reduction in production of ATP by endothelial cells subjected to oxidising stresses, so as to prevent and/or treat dysfunctions of the venous system and/or alteration to vascular permeability, and consequently to prevent the appearance and/or to reduce inaesthetic effects generated by hypoxia of endothelial cells of the human body, for example dark circles around and/or bags under the eyes and the "heavy legs" phenomenon.

This is why the first aspect of the invention is a compound with formula (I):

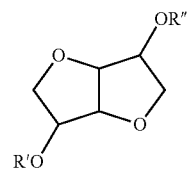

(I)

in which R' and R", are identical or different and represent:
  Either a hydrogen atom;
  Or a monovalent radical with formula (IIa):

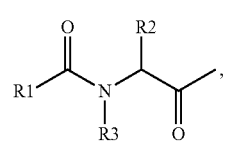

(IIa)

in which:
  R1 represents a saturated or unsaturated, linear or ramified aliphatic radical, comprising 7 to 30 carbon atoms,
  R2 represents a hydrogen atom or a radical chosen from among the methyl, isopropyl, isobutyl, 1-methyl propyl, hydroxymethyl, 1-hydroxy ethyl, thiomethyl, 2-methylthio ethyl, 4-aminobutyl, 3-guanidino propyl, 3-ureido propyl, (1-amino carbonyl)methyl, carboxy methyl, 2-carboxy ethyl, 2-(amino carbonyl)ethyl, benzyl, 4-hydroxy benzyl, 3,4-dihydroxy benzyl, [1H-indol-3-yl] methyl, (1H-imidazol-4-yl)methyl and 3-amino propyl radicals, and
  R3 represents a hydrogen atom or a methyl radical;
Or a monovalent radical with formula (IIb):

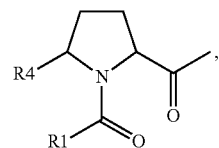

(IIb)

in which:
  R1 is such as defined in formula (IIa) and
  R4 represents a hydrogen atom or a hydroxy radical,
it being understood that at least one of the R' or R" radicals does not represent a hydrogen atom and that when the R' and R" radicals do not represent a hydrogen atom, R' and R" are identical.

According to a first particular aspect of this invention, the compound with formula (I) such as defined above and more particularly chosen from among the isosorbide esters derived from the following amino acids: glycine, alanine, serine, aspartic acid, glutamic acid, valine, threonine, arginine, lysine, proline, leucine, phenylalanine, isoleucine, histidine, tyrosine, tryptophane, asparagine, glutamine, cysteine, methionine, hydroxyproline, hydroxylysine, sarcosine and ornithine.

According to one particular aspect of this invention, its purpose is a compound with formula (I) such as defined above, in which the $R_1$ radical comprises 7 to 22 carbon atoms.

According to this particular aspect, in the definition of the radical with formula (IIa) or the radical with formula (IIb), the $R_1$—C(═O)— radical represents principally a radical chosen from among the octanoyl, decanoyl, ω-undecylenoyl, dodecanoyl, tetradecanoyl, hexadecanoyl, octadecanoyl, eicosanoyl, docosanoyl, 9-octadecenoyl, eicosenoyl, 13-docosenoyl, 9,12-octadecadienoyl and 9,12,15-octadecatrienoyl radicals.

According to another particular aspect of this invention, its purpose is a compound with formula (I) such as defined above, in which the radicals R' and R" are identical or different and represent:
  Either a hydrogen atom;
  Or a monovalent radical with formula (IIa), in which R1 and R3 are such as defined above and R2 represents a radical chosen from among the methyl, isopropyl, isobutyl, 1-methyl propyl and benzyl radicals,
  Or a monovalent radical with formula (IIb), in which R1 is a defined above and R4 represents a hydrogen atom.

According to this particular aspect of this invention, the compound with formula (I) such as defined above is chosen more particularly from among isosorbide esters derived from the following amino acids: alanine, valine, proline, leucine, phenylalanine, isoleucine.

According to another particular aspect, the purpose of the invention is a compound with formula (Ia):

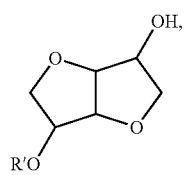

(Ia)

corresponding to formula (I) such as defined above, in which R" represents a hydrogen atom, and more particularly:
The compound with formula (Ia1):

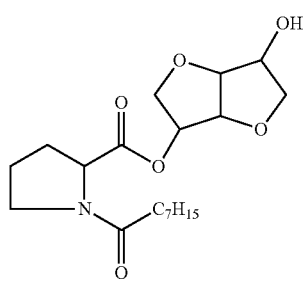

(Ia1)

The compound with formula (Ia2):

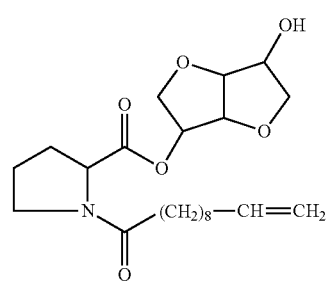

(Ia2)

The compound with formula (Ia3):

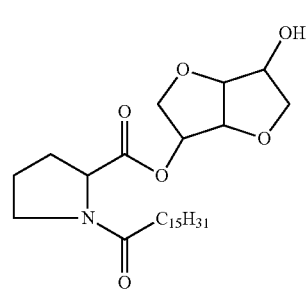

(Ia3)

The compound with formula (Ia4):

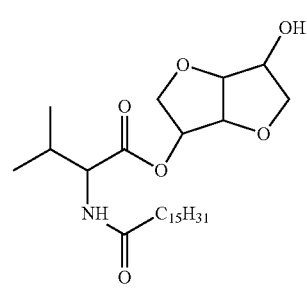

(Ia4)

Or the compound with formula (Ia5):

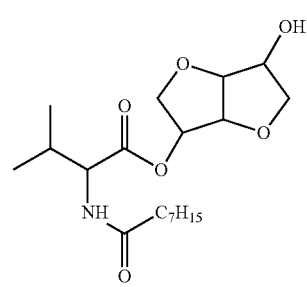

(Ia5)

According to this particular aspect of this invention, compounds with formulas (Ia1), (Ia2), (Ia3), (Ia4), and (Ia5) are chosen more particularly from among the following:
N-octanoyl prolinate of monoisosorbide,
N-(ω-undecylenoyl)prolinate of monoisosorbide, N-hexadecanoyl prolinate of monoisosorbide,
N-hexadecanoyl valinate of monoisosorbide, or
N-octanoyl valinate of monoisosorbide, respectively According to another particular aspect, the purpose of the invention is a compound with formula (Ib):

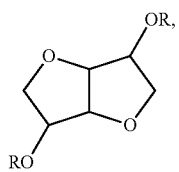

(Ib)

corresponding to formula (I) such as defined above, in which the R' and R" radicals are identical and are represented by the radical R, and more particularly:

The compound with formula (Ib1):

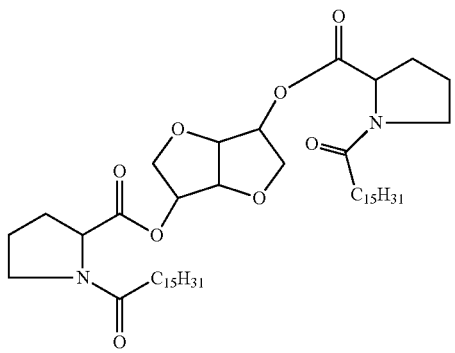

(Ib1)

The compound with formula (Ib2):

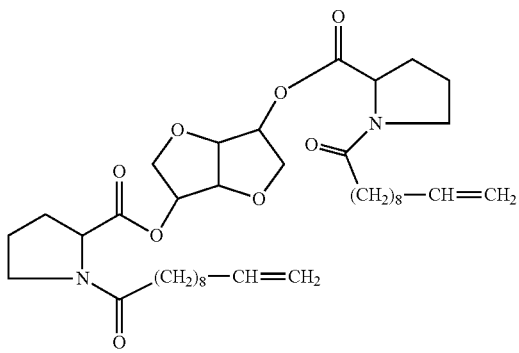

(Ib2)

The compound with formula (Ib3):

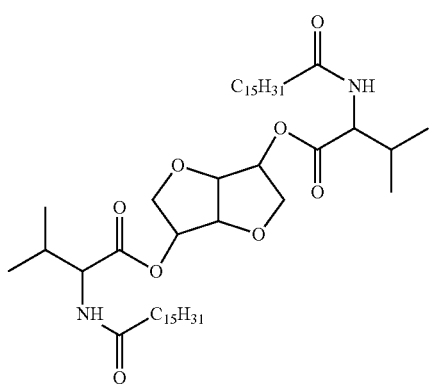

(Ib3)

The compound with formula (Ib4):

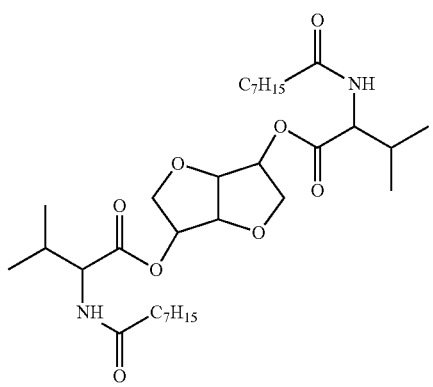

(Ib4)

Or the compound with formula (Ib5):

(Ib5)

According to this particular aspect of this invention, compounds with formulas (Ib1), (Ib2), (Ib3), (Ib4), and (Ib5), are chosen more particularly from among the following:

N-octanoyl prolinate of diisosorbide,
N-(ω-undecylenoyl)prolinate of diisosorbide,
N-hexadecanoyl prolinate of diisosorbide,
N-hexadecanoyl valinate of diisosorbide, or
N-octanoyl valinate of diisosorbide, respectively.

Another purpose of the invention is a method of preparing a compound with formula (I) such as defined above, comprising:

An esterification step a):
Either a compound with formula (IIIa):

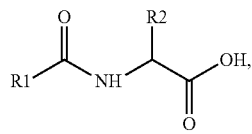
(IIIa)

in which R1 and R2 are such as defined in formula (IIa),
Or a compound with formula (IIIb):

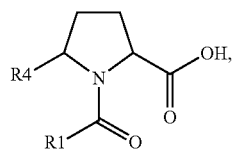
(IIIb)

in which $R_1$ and R4 are such as defined for formula (IIb), with isosorbide with formula (IV):

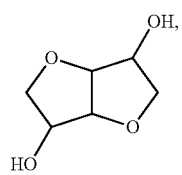
(IV)

to obtain either the compound with formula (Ia), or the compound with formula (Ib), or a mix (M) of the compound with formula (Ia) and the compound with formula (Ib); and if necessary or if desired, A step b) in which compounds with formula (Ia) and with formula (Ib) are separated starting from said mix (M) obtained in step (a).

Compounds with formulas (IIIa) and (IIIb) are known or can be synthesised by N-acylation of the corresponding α-amino acids using methods known to those skilled in the art.

In the method defined above, the molar ratio composed of formula (IIIa) or formula (IIIb) on isosorbide with formula (IV) is generally between 3:1 and 1:5, more particularly between 1:1 and 1:5, and even more particularly between 1:1 and 1:3.

In the method defined above, step b) to separate compounds with formula (Ia) from compounds with formula (Ib) is implemented using conventional separation methods known to those skilled in the art.

Another purpose of the invention is a method of preparing a compound with formula (I) such as defined above comprising:

An esterification step a1), either of a compound with formula (IIIa)

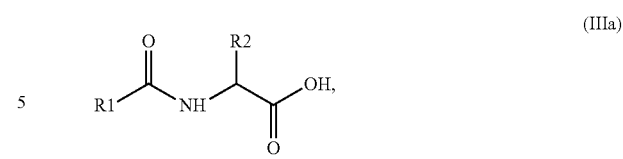
(IIIa)

in which R1 and R2 are such as defined in formula (IIa), or a compound with formula (IIIb)

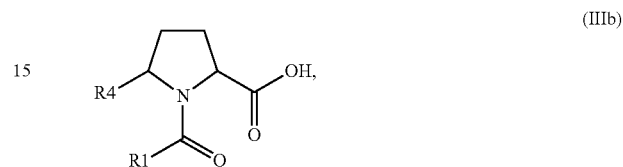
(IIIb)

in which $R_1$ and R4 are such as defined for formula (IIb), with an alcohol with formula (V):

R5-OH    (V), in which R5 represents a linear aliphatic radical comprising 1 to 4 carbon atoms, to form:
Either a compound with formula (VIa):

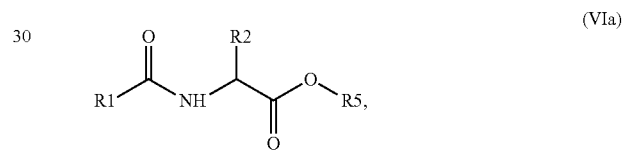
(VIa)

in which R1, R2 and R5 are such as defined above,
Or a compound with formula (VIb):

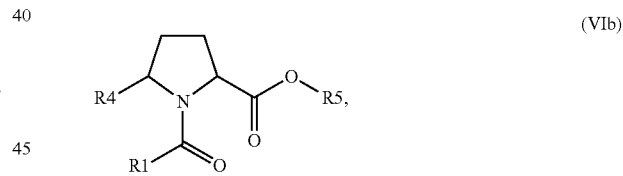
(VIb)

in which R1, R4 and R5 are such as defined above;
A step a2) for trans-esterification of the compound with formula (VIa) or the compound with formula (VIb) obtained in step a1), by reaction with the isosorbide with formula (IV), to obtain either the compound with formula (Ia) or the compound with formula (Ib), or a mix (M) of the compound with formula (Ia) and the compound with formula (Ib); and if necessary or if desired,
Implementation of step b).

In the method according to the invention such as defined above, step a1) is usually done at a temperature of about between 60° C. and 120° C. under an inert gas, in the presence of an acid catalytic system. An acid catalytic system refers to strong acids such as sulphuric acid, hydrochloric acid, phosphoric acid, nitric acid, hypophosphorous acid, methanesulfonic acid, para-toluene sulfonic acid, trifluoromethane sulfonic acid or acid ion exchanging resins.

In step a1) of the method disclosed by this invention such as defined above, the molar ratio composed of formula (IIIa) or formula (IIIb) on alcohol with formula (V) is usually between 1:1 and 1:10, more particularly between 1:1 and 1:8, and even more particularly between 1:2 and 1:8.

In the method disclosed by this invention such as defined above, step a2) for trans-esterification of the ester with formula (VIa) and/or with formula (VIb) obtained in step a1) is usually done at a temperature of about between 80° C. and 180° C., more particularly between 100° C. and 150° C., even more particularly between 120° C. and 150° C., under inert gas, and in the presence of an acid catalytic system as described above and with vacuum distillation of alcohol with formula (VI) formed in-situ.

In step a2) of the method, the molar ratio composed of formula (VIIa) and/or formula (VIIb) on isosorbide with formula (V) is between about 3:1 and 1:5, more particularly between 1:1 and 1:5, and even more particularly between 1:1 and 1:3.

Another purpose of the invention is a composition (C1) comprising the following for 100% of its mass:
   From 99% by mass to 20% by mass, more particularly from 99% by mass to 50% by mass and more particularly from 95% by mass to 75% by mass of at least one compound with formula (Ia) such as defined above, and
   From 1% by mass to 80% by mass, more particularly from 1% by mass to 50% by mass, and even more particularly from 5% by mass to 25% by mass of at least one compound with formula (Ib) such as defined above.

According to one particular aspect, in the composition (C1) disclosed by this invention, the compound (Ia) is selected from among compounds with formula (Ia1), (Ia2), (Ia3), (Ia4), or (Ia5) such as defined above and the compound (Ib) is selected from among compounds with formula (Ib1), (Ib2), (Ib3), (Ib4) or (Ib5) such as defined above.

Composition ($C_1$) according to the invention may be prepared by various methods.

A first method of preparing composition ($C_1$) disclosed by this invention consists of mixing the compound with formula (Ia) such as defined above or the mix of compounds with formula (Ia) with the compound with formula (Ib) such as defined above or the mix of compounds with formula (Ib), in the required proportions by mass such as defined above.

A second method of preparing composition ($C_1$) disclosed by this invention consists of using the method of preparing the compound with formula (I) as described above, allowing isosorbide with formula (IV) to react with the compound with formula (IIIa) or with formula (IIIb) or a mix of compounds with formula (IIIa) and with formula (IIIb), in the required proportions.

A third method of preparing the composition (C1) disclosed by this invention consists of using the variant of the method of preparing the compound with formula (I) such as described above, allowing isosorbide with formula (IV) to react with the compound with formula (VIa) or with formula (VIb) or a mix of compounds with formula (VIa) and with formula (VIb) in the required proportions.

Another purpose of the invention is use of the compound with formula (I) or the composition (C1) such as defined above as cosmetic active constituent, in order to prevent and/or limit inaesthetic effects generated by hypoxia of endothelial cells of the human body and more particularly inaesthetic effects generated by dark circles or bags under the eyes and/or heavy legs.

The compound with formula (I) and composition (C1) according to this invention may be administered orally, topically or parenterally.

Another purpose of the invention is a cosmetic formulation for topical use characterised in that it comprises at least one cosmetically acceptable excipient and an effective quantity of the compound with formula (I) or the composition (C1) such as defined above.

The expression "for topical use" used in the definition of the cosmetic formulation as described above means that said formulation is used by application on the skin, either by direct application in the case of a cosmetic formulation or indirect application for example in the case of a product for body care in the form of a textile or paper wipe and sanitary products designed to come in contact with the skin.

According to the European Economic Community Council directive No. 76/768/EEC Jul. 27, 1976 modified by directive No. 93/35/EEC Jun. 14, 1993, the expression "cosmetically acceptable" used in the definition of the cosmetic formulation such as described above, means that said formulation comprises any substance or preparation that is intended to come into contact with various parts of the human body (epiderm, hair and capillary system, nails, lips and genitals) or with the teeth or with mouth mucous membranes, exclusively and mainly with the aim of cleaning them, perfuming them, modifying the appearance and/or modifying body odours and/or protecting them or to keep them in good condition.

Finally, another purpose of the invention is a non-therapeutic method of treating the human skin intended to prevent the appearance and/or to reduce dark circles and/or bags under the eyes and/or the heavy legs phenomenon comprising at least one step to apply an effective quantity of the cosmetic formulation for topical use such as defined above on said human skin.

An effective quantity of compound with formula (I) such as defined above or a composition (C1) such as defined above in the cosmetic formulation for topical use and/or in the medicine such as defined above intended to prevent and/or treat hypoxia of endothelial cells of the human body, and more particularly to prevent the appearance and/or to reduce dark circles and/or bags under the eyes and/or the heavy legs phenomenon, means for 100% of the mass of said cosmetic formulation for topical and/or medical use, the quantity of between 0.1% and 5% by mass, more particularly between 0.1% and 3% by mass, and even more particularly between 0.5% and 2.% by mass of compound with formula (I) or composition (C1).

In the non-therapeutic treatment method as described above, the cosmetic formulation for topical use is spread on the surface of the skin to be treated and the skin is then massaged for a few moments.

The cosmetic formulation for topical use disclosed by this invention is generally in the form of dilute aqueous or hydro-alcoholic solutions, or in the form of single or multiple emulsions such as water in oil (W/O), oil in water (O/W) or water in oil in water (W/O/W) emulsions, in which the oil may be vegetable or mineral, or in the form of a powder. They may also be dispersed or impregnated on textile or on non-woven materials like wipes, paper towels or clothes.

In general, the compound with formula (I) or the composition (C1) is associated with many types of additives or active constituents used in the cosmetic formulation such as defined above and disclosed by this invention, as either fatty bodies, organic solvents, thickeners, gelling agents, softeners, foaming and/or detergent surface active agents, superfatting agents, thickening and/or gelling surface active agents, antioxidants, opacifiers, stabilisers, foams, perfumes, emulsion surface active agents, hydrotropic agents, plastifiers, superfatting agents, texture agents, pigments, sequestrators, chelators, preservatives, essential oils, colouring materials, hydrophilic or lipophilic active agents, moisturisers, perfumes, inorganic or organic solar filters, mineral fillers or any other ingredient usually used in cosmetics.

Examples of oils that can be associated with the compound with formula (I) or the composition (C1) in the cosmetic formulations for topical use disclosed by this invention include mineral oils such as paraffin oil, vaseline oil, isoparaffins or white mineral oils, oils from animal origin such as squalene or squalane, vegetable oils such as sweet almond oil, copra oil, ricin oil, jojoba oil, olive oil colza oil, peanut oil, sunflower oil, wheat germ oil, corn germ oil, soya oil, cotton oil, alfalfa oil, poppy seed oil, pumpkin oil, evening primrose oil, millet oil, barley oil, rye oil, safflower oil, bancoulier oil, passion flower oil, hazelnut oil, palm oil, shea butter, apricot kernel oil, calophyllum oil, sisymbrium oil, avocado oil, calendula oil; ethoxylated vegetable oils; synthetic oils like fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propyleneglycol dicaprylate, esters derived from lanolic acid such as isopropyl lanolate, isocetyl lanolate, monoglycerides, diglycerides and triglycerides of fatty acids such as glycerol triheptanoate, alkylbenzoates, polyalphaolefins, polyolefins such as polyisobutene, synthetic isoalkanes such as isohexadecane, isododecane, perfluorated oils and silicone oils. The most useful of these include more particularly dimethylpolysiloxanes, methylphenylpolysiloxanes, silicones modified by amines, silicones modified by fatty acids, silicones modified by alcohols, silicones modified by alcohols and fatty acids, silicones modified by polyether groups, modified epoxy silicones, silicones modified by fluoride groups, cyclic silicones and silicones modified by alkyl groups.

Other fatty materials that can be associated with the compound with formula (I) or composition (C1) in the cosmetic formulations for topical use disclosed by this invention include fatty alcohols and fatty acids.

Examples of waxes that can be associated with the compound with formula (I) or composition (C1) in cosmetic formulations for topical use disclosed by this invention include for example beeswax, carnauba wax, candelilla wax, ouricoury wax, Japan wax, cork fibre wax or sugar cane wax, paraffin waxes, lignite waxes, microcrystalline waxes, lanolin wax, ozokerite, polyethylene wax; hydrogenated oils, silicone waxes, vegetable waxes, fatty alcohols and fatty acids solid at ambient temperature, glycerides solid at ambient temperature.

Examples of thickening and/or emulsioning polymers that can associated with the compound with formula (I) or composition (C1) in cosmetic formulations for topical use disclosed by this invention include for example homopolymers or copolymers of acrylic acid or derivatives of acrylic acid, homopolymers or copolymers of acrylamide, homopolymers or copolymers of acrylamide derivatives, homopolymers or copolymers of acrylamidomethyl propanesulfonic acid, vinyl monomer, trimethylaminoethylacrylate chloride, hydrocolloïds from vegetable or biosynthetic origin, for example xanthane gum, karaya gum, carraghenates, alginates; silicates; cellulose and its derivatives, starch and its hydrophilic derivatives; polyurethanes.

Polyelectrolyte type polymers that can be associated with the compound with formula (I) or composition (C1) in the cosmetic formulations for topical use disclosed by this invention include for example copolymers of acrylic acid and -2-methyl-[(1-oxo-2-propenyl)amino]1-propane sulfonic acid (AMPS), copolymers of acrylamide and -2-methyl-[(1-oxo-2-propenyl)amino]1-propane sulfonic acid, copolymers of -2-methyl-[(1-oxo-2-propenyl)amino]1-propane sulfonic acid and (2-hydroxyethyl)acrylate, homopolymer of -2-methyl-[(1-oxo-2-propenyl)amino]1-propanesulfonic acid, homopolymer of acrylic acid, copolymers of acryloyl ethyl trimethyl ammonium chloride and acrylamide chloride, copolymers of AMPS and vinylpyrolidone, copolymers of acrylic acid and alkyl acrylates in which the carbon chain comprises between ten and thirty atoms of carbon, copolymers of AMPS and alkyl acrylates in which the carbon chain comprises between ten and thirty carbon atoms. Such polymers are marketed by the applicant under the names SIMULGEL™ EG, SEPIGEL™ 305, SIMULGEL™ NS, SIMULGEL™ 800 and SIMULGEL™ A respectively.

Examples of emulsifying agents that can be associated with the compound with formula (I) or composition (C1) in cosmetic formulations for topical use disclosed by this invention include for example fatty acids, ethoxylated fatty acids, esters of fatty acids and of sorbitol, esters of ethoxylated fatty acids, polysorbates, esters of polyglycerol, ethoxylated fatty alcohols, sucrose esters, alkylpolyglycosides, sulphated and phosphated fatty alcohols or mixes of alkylpolyglycosides and fatty alcohols disclosed in French patent applications 2 668 080, 2 734 496, 2 756 195, 2 762 317, 2 784 680, 2 784 904, 2 791 565, 2 790 977, 2 807 435 and 2 804 432.

Examples of foaming surface active agents and/or detergents that can be associated with the compound with formula (I) or composition (C1) in cosmetic formulations for topical use disclosed by this invention include anionic, cationic, amphoteric or non-ionic surface active agents normally acceptable in this activity field.

Anionic surface active agents that can be associated with the compound with formula (I) or composition (C1) in cosmetic formulations for topical use disclosed by this invention, include particularly salts of alkaline metals, salts of alkali earth metals: ammonium salts, amine salts, amino alcohol salts of the following compounds: alkylether sulfates, alkylsulfates, alkylamidoethersulfates, alkylarylpolyethersulfates, monoglyceride sulfates, alpha-olefinesulfonates, paraffin sulfonates, alkylphosphates, alkyletherphosphates, alkylsulfonates, alkylamidesulfonates, alkylarylsulfonates, alkylcarboxylates, alkylsulfosuccinates, alkylethersulfosuccinates, alkylamidesulfosuccinates, alkylsulfoacetates, alkylsarcosinates, acyl isethionates, N-acyltaurates, acyllactylates.

Anionic surface active agents that can be associated with the compound with formula (I) or composition (C1) in cosmetic formulations for topical use disclosed by this invention, also include N-acylated derivatives of amino acids, peptides, proteins in which the acyl chain comprises 8 to 16 carbon atoms; fatty acid salts, possibly hydrogenated copra oil acid salts.

Amphoteric surface active agents that can be associated with the compound with formula (I) or composition (C1) in cosmetic formulations for topical use disclosed by this invention include particularly alkylbetaines, alkylamidobetaines, sultaines, alkylamidoalkylsulfobetaines, imidazoline derivatives, phosphobetaines, amphopolyacetates and amphopropionates.

Cationic surface active agents that can be associated with the compound with formula (I) or composition (C1) in cosmetic formulations for topical use disclosed by this invention, include particularly derivatives of quaternary ammoniums.

Non-ionic surface active agents that can be associated with the compound with formula (I) or composition (C1) in cosmetic formulations for topical use disclosed by this invention, include particularly alkylpolyglycosides in which the alkyl chain comprises 8 to 16 carbon atoms, derivatives of ricin oil, polysorbates, copra amides, N-alkylamines, amine oxides.

Examples of texture agents that can be associated with the compound with formula (I) or composition (C1) in cosmetic formulations for topical use disclosed by this invention, include for example derivatives of N-acylated amino acids, for example such as lauroyl lysine marketed under the name AMINOHOPE™ LL by the AJINOMOTO Company, octenyl starch succinate marketed under the name DRYFLO™ by the NATIONAL STARCH Company, myristyl polyglucoside marketed by SEPPIC under the name MONTANOV 14, cellulose fibres, cotton fibres, chitosan fibres, talc, sericite, mica.

Examples of opicifying agents and/or nacrous agents that can be associated with the compound with formula (I) or composition (C1) in cosmetic formulations for topical use disclosed by this invention, include for example sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate, fatty alcohols.

Examples of thickening and/or gelling surface active agents that can be associated with the compound with formula (I) or composition (C1) in cosmetic formulations for topical use disclosed by this invention, include:

- Fatty esters of possibly alkoxylated alkylpolyglycosides, and particularly esters of ethoxylated methylpolyglucoside such as PEG 120 methyl glucose trioleate and PEG 120 methyl glucose dioleate marketed under the names GLUCAMATE™ LT and GLUMATE™ DOE120 respectively.
- Alkoxylated fatty esters such as PEG 150 pentaerythrytyl tetrastearate marketed under the name CROTHIX™ DS53, PEG 55 propylene glycol oleate marketed under the name ANTIL™ 141.
- Polyalkylene glycol carbamates with fatty chains such as PPG 14, laureth isophoryl dicarbamate marketed under the name ELFACOS™ T211, PPG 14 palmeth 60 hexyl dicarbamate marketed under the name ELFACOS™ GT2125.

Examples of solar filters that can be associated with the compound with formula (I) or composition (C1) in cosmetic formulations for topical use disclosed by this invention, include all those mentioned in modified cosmetic directive 76/768/EEC in Appendix VII.

Examples of active constituents that can be associated with the compound with formula (I) or composition (C1) in cosmetic formulations for topical use disclosed by this invention, include compounds with lightening or depigmenting action for example such as arbutine, kojic acid, hydroquinone, ellagic acid, vitamin C, magnesium ascorbyl phosphate, extracts of polyphenols, derivatives of glycosylated polyphenols such as Rosmarinyl glucoside, grape extracts, pine extracts, wine extracts, olive extracts, pomace extracts, N-acylated proteins, N-acylated peptides, N-acylated amino acids, partial hydrolysates of N-acylated proteins, amino acids, peptides, total protein hydrolysates, partial protein hydrolysates, polyols (for example glycerine or butylene glycol), urea, pyrrolidonecarboxylic acid or derivatives of this acid, glycyrrhetinic acid, alpha-bisabolol, sugars or derivatives of sugars, polysaccharides or their derivatives, hydroxy-acids for example lactic acid, vitamins, derivatives of vitamins such as Retinol, vitamin E and its derivatives, minerals, enzymes, co-enzymes, such as Coenzyme Q10, hormones or "hormone like", extracts of soya for example Raffermine™, wheat extracts for example Tensine™ or Gliadine™, vegetable extracts such as tanin-rich extracts, isoflavone-rich extracts or terpene-rich extracts, extracts of fresh water algae or sea algae, essential waxes, bacterial extracts, minerals, lipids in general, lipids such as ceramids or phospholipids, agents with a slimming action such as caffeine or derivatives of it such as quinoa extract marketed under the name ADIPOLESS™, such as Canadian hemlock extract marketed under the name SERENIKS™ 207, such as the composition comprising Lauroyl Proline marketed under the name ADIPOSLIM™, agents with an anti-microbial activity or a purifying action for oily skins such as LIPACIDE™ PVB, constituents with an energising or stimulating property such as SEPITONIC™ M3 or Physiogenyl™ panthenol and its derivatives such as SEPICAP™ MP, anti-aging constituents such as SEPILIFT™ DPHP, LIPACIDE™ PVB, SEPIVINOL™, SEPIVITAL™, hydrating agents such as SEPICALM™ S, SEPICALM™ VG and SEPILIFT™ DPHP, anti-photo aging constituents, agents protecting the integrity of the dermo-epidermal junction, agents increasing synthesis of components in the extracellular matrix, agents with a slimming effect such as caffeine, theophylline, AMPc, green tea, sage, gingko biloba, ivy, horse chestnut, bamboo, ruscus, butcher's broom, centella asiatica, heather, ulmaine, fucus, rosemary, willow, constituents creating a "warming" sensation on the skin such as skin microcirculation activators (for example nicotinates) or products creating a feeling of "freshness" on the skin (for example menthol and derivatives of it).

Another purpose of the invention is a compound with formula (I) or composition (C1) such as defined above for implementation of a therapeutic treatment method of a human or animal body and more particularly a compound with formula (I) or composition (C1) such as defined above, for use in a method for therapeutic treatment of hypoxia of endothelial cells of the human or animal body, and more particularly a method for therapeutic treatment of dark circles or bags under the eyes, and/or heavy legs.

The following experimental study illustrates but does not limit the invention.

EXAMPLES FOR PREPARATION OF COMPOUNDS WITH FORMULA (I) ACCORDING TO THE INVENTION

Example 1

Preparation of a Composition A Comprising Compounds with Formulas (Ia1) and (Ib1)

400.0 grams of proline, namely a molar equivalent are introduced into a mix of 1600 grams composed of 1440 grams of water and 160 grams of isopropanol, in a double skin glass reactor in which a coolant fluid is circulating, provided with an efficient stirring and a nitrogen bubbling device through the bottom of the reactor at a temperature of 20° C. The pH of the medium thus prepared is adjusted to a pH value of 10 by adding a 30% soda solution. 450 grams of octanoyl chloride, namely 0.8 molar equivalent, are then added progressively to the medium at a temperature of between 20° C. and 30° C., so as to control exothermicity; a 30% soda solution is added at the same time to keep the value of the pH of the medium to a value between 10 and 10.5.

After adding octanoyl chloride, the reaction medium is kept stirred for a duration of 2 hours. The reaction medium is then heated to 70° C. under stirring and a quantity of 724 grams of an acid solution of 75% phosphoric acid is then progressively introduced so that the pH of the reaction medium is equal to about 2.0. Stirring is stopped and the aqueous phase of the decanted medium is then drawn off. The organic phase remaining in the reactor is then washed with a quantity of 3000 grams of water at ambient temperature while stirring. The aqueous phase is drawn off through the bottom of the reactor and the washing phase as described above is repeated once again. After washing, the organic phase is dried by distillation of residual water under a vacuum.

A quantity of 90 grams of isosorbide namely a molar equivalent of isosorbide, is introduced into the reactor containing 161 grams of the dried reaction medium, stirred and heated to a temperature of 120° C. When the mix is well dispersed, a quantity of 0.6 grams of 98% sulphuric acid is introduced into the reactor and the resulting mix is heated to a temperature of 125° C., under partial vacuum with regular nitrogen bubbling introduced through the bottom of the reactor. The reaction mix is then held at 125° C. for 24 hours while stirring and is then neutralised by the addition of a 30% soda solution to obtain a pH of 5% of the reaction medium between 3.0 and 6.0. The reaction medium is then drained and the measured analytic characteristics of the composition A are as follows:
Acid index (using NFT 60-204)=85.8
pH 5% of composition A in water (using the method NFT 73-206)=3.3
Hydroxyl index (according to U.S. Pharmacopeia XXI NF XVI 01/011985)=214.7
Ester index (calculated by taking the difference between the saponification index measured using the method NFT 60-110 and the acid index measured using the method NFT 60-204)= 65.3

Example 2

Preparation of a Composition B Comprising Compounds with Formulas (Ia2) and (Ib2)

The procedure in the method described in example 1 is used for a molar equivalent of proline, 0.8 molar equivalent of undecylenoyl chloride and a molar equivalent of isosorbide to obtain composition B with the following analytic characteristics:
Acid index (using NFT 60-204)=78.4
pH 5% of composition B in water (using the method NFT 73-206)=4.2
Hydroxyl index (according to U.S. Pharmacopeia XXI NF XVI 01/011985)=191.7
Ester index (calculated by taking the difference between the saponification index measured using the method NFT 60-110 and the acid index measured using the method NFT 60-204)= 67.8

Example 3

Preparation of a Composition D Comprising Compounds with Formulas (Ia3) and (Ib3)

The procedure in the method described in example 1 is used for a molar equivalent of proline, 0.8 molar equivalent of hexadecanoyl chloride and a molar equivalent of isosorbide to obtain composition D with the following analytic characteristics:
Acid index (using NFT 60-204)=64.1
pH 5% of composition D in water (using method NFT 73-206)=4.8
Hydroxyl index (according to U.S. Pharmacopeia XXI NF XVI 01/011985)=166.9
Ester index (calculated by taking the difference between the saponification index measured using the method NFT 60-110 and the acid index measured using the method NFT 60-204)= 55.4.

Example 4

Preparation of a Composition E Comprising Compounds with Formulas (Ia4) and (Ib4)

The procedure in the method described in example 1 is used for a molar equivalent of valine, 0.8 molar equivalent of hexadecanoyl chloride and a molar equivalent of isosorbide to obtain composition E with the following analytic characteristics:
Acid index (using NFT 60-204)=12.3
pH 5% of composition E in water (using the method NFT 73-206)=7.5
Hydroxyl index (according to U.S. Pharmacopeia XXI NF XVI 01/011985)=100.2
Ester index (calculated by taking the difference between the saponification index measured using the method NFT 60-110 and the acid index measured using the method NFT 60-204)= 96.2

Example 5

Preparation of a Composition F Comprising Compounds with Formulas (Ia5) and (Ib5)

The procedure in the method described in example 1 is used for a molar equivalent of proline, 0.8 molar equivalent of octanoyl chloride and a molar equivalent of isosorbide to obtain composition F with the following analytic characteristics:
Acid index (using NFT 60-204)=43.7
pH 5% of composition F in water (using the method NFT 73-206)=4.0
Hydroxyl index (according to U.S. Pharmacopeia XXI NF XVI 01/011985)=181.4
Ester index (calculated by taking the difference between the saponification index measured using the method NFT 60-110 and the acid index measured using the method NFT 60-204)= 99.3

Evaluation of the Effect of Compounds and Compositions According to the Invention on the Production of Intracellular ATP in Cultures of Endothelial Cells Having being Subjected to an Oxidising Stress Protocol HUVEC (Human Umbilical Vein Endothelial Cells) cells in the R3 passage are seeded with 2000 cells/wells in plates comprising 96 wells.

The cells are then cultivated in the EGM-2 (Endothelial Growth Medium) medium, marketed by the Lonza Company for 7 days at a temperature of 37° C. in 5% $CO_2$.

The culture media are then replaced by an EGM-2 medium, containing dilutions of compounds and compositions to be tested.

Controls (T) are also prepared by replacing culture media by the EGM-2 medium alone.

Cells present in the EGM-2 medium and associated with dilutions of compounds and compositions to be tested as well as the controls (T) are then incubated for a period of 24 hours at a temperature of 37° C.

Following this incubation, the media of cells associated with dilutions of compounds and compositions to be tested and the media of controls (T) are replaced by an EGM-2 medium supplemented with oxygenated water at a concentration of 0.8 millimoles per liter.

In the following the term "controls (T1)" is used to refer to controls (T) supplemented with oxygenated water and "controls (T)" is used to refer to controls (T) not supplemented with oxygenated water.

Cells associated with dilutions of compounds and compositions to be tested, controls (T) and controls (T1) are then incubated for 10 minutes at a temperature of 37° C., and then rinsed with PBS (Phosphate Buffer Saline).

The quantity of intracellular ATP and the quantity of proteins produced by cells associated with dilutions of compounds and compositions to be tested, controls (T) and controls (T1) are evaluated after lysis of molecular cells in the presence of a lysis buffer.

The quantity of ATP is quantified by the luminometric method, implemented using a luminometer plates reader brandname FLUOROSKAN ASCENT FL™ marketed by the LABSYSTEMS Company, and the quantification of proteins is done using the BCA method. With this method dosed ATP quantities can be normalised and the cytotoxycity of each experimental condition can be evaluated.

A cytotoxicity threshold has been fixed at 80% for the control group.

The results are expressed in millimoles of ATP produced per milligram of proteins produced and the statistical study of the results was made using Student's bilateral unequal variance T test.

The effects evaluated on cells associated with dilutions of compounds and compositions to be tested, controls (T) and controls (T1) were done on two independent experiments and the results presented correspond to the average of the two tests.

The most restrictive statistics were applied for each experimental condition. The results obtained are given in Table 1 below:

TABLE 1

| Tested composition | Concentration (% p/v) relative to the dry extract | Quantity of ATP produced (mmoles of ATP/mg of proteins) |
|---|---|---|
| Control (T) | — | 0.045 |
| Control (T1) | — | 0.016 |
| Composition A | 0.0001% | 0.021 |
| Composition B | 0.000025% | 0.022 |
| Composition B | 0.00005% | 0.023 |
| Composition D | 0.00005% | 0.025 |
| Composition D | 0.0005% | 0.022 |
| Composition E | 0.00005% | 0.020 |
| Composition F | 0.00005% | 0.021 |
| Composition F | 0.0005% | 0.023 |

The oxidising stress procured by the addition of oxygenated water on control cells (T) induces a reduction of 64% of the ATP produced by the endothelial cells (control cells (T1). This result thus validates the experimental test conditions applied.

When the endothelial cells are associated with composition A, the quantity of ATP produced by said endothelial cells is 31.25% more than with the control cells (T1) subjected to the same oxidising stress.

When the endothelial cells are associated with compositions A to F, quantities of ATP produced by said endothelial cells is between 25% (for composition E) and 56.2% (composition D tested at 0.00005%) higher than with control cells (T1) subjected to the same oxidising stress.

None of the tested compositions induced any significant cytotoxicity according to the BCA test used with the "BC-assay" kit marketed by the Interchim Company.

The result is that compositions according to the invention comprising compounds according to the invention can slow the production of ATP by endothelial cells subjected to oxidising stresses.

BIBLIOGRAPHIC REFERENCES MENTIONED IN THE DESCRIPTION (1) Chang et al.: "Aging and survival of cutaneous microvasculature", J. Invest Dermatol. 2002 May; 118(5):752-8.

(2) Chung et al.: "Differential effects of photoaging vs intrinsic aging on the vascularization of human skin" Arch. Dermatol. 2002 November; 138(11):1437-42.

(3) Toyoda et al.: "Ultrastructural characterization of microvasculature in photoaging" J. Dermatol Sci. 2001 August; 27 Suppl 1:S32-41.

(4) Janssens, "effect of venotropic drugs on the respiratory activity of isolated mitochondria and in endothelial cells", in British Journal of Pharmacology (2000) 130, 1513-1524

(5) M. Okada et al., J. Appl. Polym. Sci., 2001, 81(11), pages 2721-2734.

(6) Z. Gomurashvili et al., J. Macromol. Sci., Pure Appl. Chem., 2000, A37(3), 215-227.

The invention claimed is:

1. A compound with formula (I):

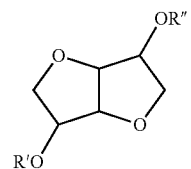

(I)

wherein R' and R", are identical or different and represent a moiety selected from the group consisting of:
(a) a hydrogen atom;
(b) a monovalent radical with formula (IIa):

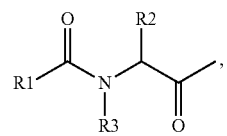

(IIa)

wherein:
R1 represents a saturated or unsaturated, linear or ramified aliphatic radical, comprising 7 to 30 carbon atoms,
R2 represents a hydrogen atom or a radical selected from the group consisting of methyl, isopropyl, isobutyl, 1-methyl propyl, hydroxymethyl, 1-hydroxy ethyl, thiomethyl, 2-methylthio ethyl, 4-aminobutyl, 3-guanidino propyl, 3-ureido propyl, (1-amino carbonyl)methyl, carboxy methyl, 2-carboxy ethyl, 2-(amino carbonyl) ethyl, benzyl, 4-hydroxy benzyl, 3,4-dihydroxy benzyl, [1H-indol-3-yl]methyl, (1H-imidazol-4-yl) methyl and 3-amino propyl radicals, and
R3 represents a hydrogen atom or a methyl radical; and (c) a monovalent radical with formula (IIb):

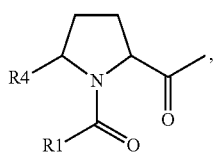

wherein:
R1 is a saturated or unsaturated, linear or ramified aliphatic radical, comprising 7 to 30 carbon atoms, and
R4 represents a hydrogen atom or a hydroxy radical,
at least one of the R' or R" radicals does not represent a hydrogen atom and that when the R' and R" radicals do not represent a hydrogen atom, R' and R" are identical.

2. The compound with formula (I) such as defined in claim 1, wherein the $R_1$ radical comprises 7 to 22 carbon atoms.

3. The compound with formula (I) such as defined in claim 1, wherein radicals R' and R" are identical or different and represent: a moiety selected from the group consisting of:
(a) a hydrogen atom;
(b) a monovalent radical with formula (IIa), wherein R2 represents a radical selected from the group consisting of methyl, isopropyl, isobutyl, 1-methyl propyl and benzyl radicals, and
(c) a monovalent radical with formula (IIb), wherein R4 represents a hydrogen atom.

4. A compound with formula (Ia):

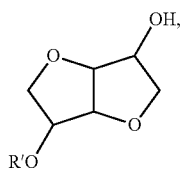

corresponding to formula (I) such as defined in claim 1, wherein R" represents a hydrogen atom.

5. A compound with formula (Ib):

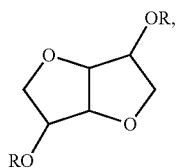

corresponding to formula (I) such as defined in claim 1, wherein the R' and R" radicals are identical and are represented by the radical R.

6. A method of preparing a compound with formula (I) such as defined in claim 1, comprising:
An esterification step a) of a compound selected from the group consisting of:

(i) a compound with formula (IIIa):

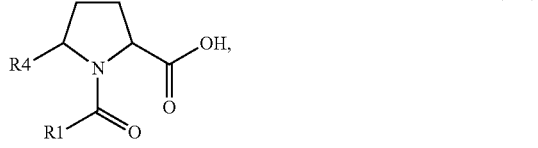

wherein R1 and R2 are such as defined in formula (IIa), and
(ii) a compound with formula (IIIb):

wherein $R_1$ and R4 are such as defined for formula (IIb)
with isosorbide with formula (IV):

to obtain either the compound with formula (Ia), or the compound with formula (Ib), or a mix (M) of the compound with formula (Ia) and the compound with formula (Ib); and optionally,
A step b) wherein compounds with formula (Ia) and with formula (Ib) are separated starting from said mix (M) obtained in step (a).

7. A method for preparing a compound with formula (I) such as defined in claim 1 comprising:
An esterification step a1), of a compound selected form the group consisting of (i) a compound with formula (IIIa)

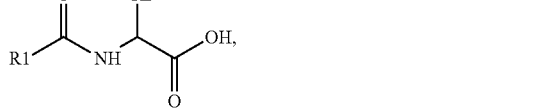

wherein R1 and R2 are such as defined in formula (IIa), and
(ii) a compound with formula (IIIb)

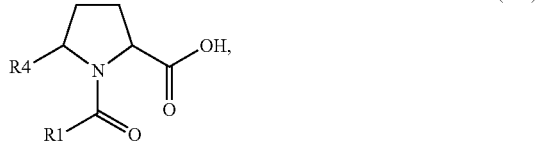

wherein R₁ and R4 are such as defined for formula (IIb), with an alcohol with formula (V):

R5-OH    (V), wherein R5 represents a linear aliphatic radical comprising 1 to 4 carbon atoms, to form one of:
(1) a compound with formula (VIa):

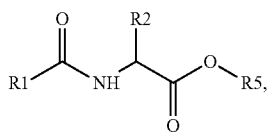

wherein R1, R2 and R5 are such as defined above, and
(2) a compound with formula (VIb):

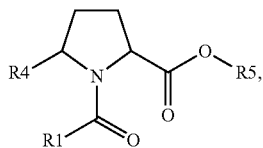

wherein R1, R4 and R5 are such as defined above;
A step a2) for trans-esterification of the compound with formula (VIa) or the compound with formula (VIb) obtained in step a1), by reaction with the isosorbide with formula (IV), to obtain either the compound with formula (Ia) or the compound with formula (Ib), or a mix (M) of the compound with formula (Ia) and the compound with formula (Ib); and optionally,
A step b) wherein compounds with formula (Ia) and with formula (Ib) are separated starting from said mix (M) obtained in step a2).

8. A compound (C1) comprising for 100% of its mass comprising compounds according to claim 1:
(i) From 99% by mass to 20% by mass of at least one compound with formula (Ia)

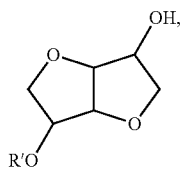

corresponding to formula (I) in which R" represents a hydrogen atom and R' is one of the moieties (b) or (c); and
From 1% by mass to 80% by mass of at least one compound with formula (Ib):

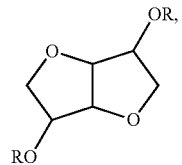

corresponding to formula (I), in which the R' and R" radicals are identical and are both moiety (b) or moiety (c), represented by the radical R.

9. A cosmetic formulation for topical use comprising at least one cosmetically acceptable excipient and an effective quantity of the compound with formula (I) as defined in claim 1.

10. A cosmetic formulation for topical use comprising at least one cosmetically acceptable excipient and an effective quantity of the composition (C1) as defined in claim 8.

11. A method for therapeutic treatment of the human or animal body suffering from visible signs of dysfunctions of the venous system and/or alteration to vascular permeability of the skin, comprising administering to a human or animal in need thereof an effective amount of a compound with formula (I) as defined in claim 1.

12. A method for therapeutic treatment of the human or animal body suffering from visible signs of dysfunctions of the venous system and/or alteration to vascular permeability of the skin, comprising administering to a human or animal in need thereof an effective amount of the composition (C1) as defined in claim 8.

13. A method for therapeutic treatment of hypoxia of endothelial cells of the human or animal body, comprising administering to a human or animal in need thereof an effective amount of a compound with formula (I) as defined in claim 1.

14. The method according to claim 13, wherein the therapeutic treatment of hypoxia of endothelial cells is the therapeutic treatment of dark circles around or bags under the eyes, and/or heavy legs.

15. A method for therapeutic treatment of hypoxia of endothelial cells of the human or animal body, comprising administering to a human or animal in need thereof an effective amount of a composition (C1) as defined in claim 8.

16. The method according to claim 15, wherein the therapeutic treatment of hypoxia of endothelial cells is the therapeutic treatment of dark circles around or bags under the eyes, and/or heavy legs.

* * * * *